United States Patent [19]

Perry

[11] Patent Number: 4,641,638

[45] Date of Patent: Feb. 10, 1987

[54] SEXUAL ERECTION PROTHESIS AND METHOD OF USE

[76] Inventor: Robert D. Perry, 16065 Perry Heights Dr., Riverside, Calif. 92504

[21] Appl. No.: 786,226

[22] Filed: Oct. 10, 1985

[51] Int. Cl.⁴ .............................................. A61F 5/41
[52] U.S. Cl. .................................................... 128/79
[58] Field of Search ........................ 128/79, DIG. 20

[56] References Cited

U.S. PATENT DOCUMENTS

| | | | |
|---|---|---|---|
| 2,378,795 | 6/1945 | Rupe | 128/79 |
| 2,533,924 | 12/1950 | Foley | 128/79 |
| 2,686,519 | 8/1954 | Westerman | 128/79 |
| 2,823,668 | 2/1958 | Van Court et al. | 128/DIG. 20 |
| 3,401,687 | 9/1968 | Hood | 128/79 |
| 3,421,504 | 1/1969 | Gibbons | 128/79 |
| 3,495,589 | 2/1970 | Clement | 128/79 |
| 3,683,901 | 8/1972 | Wegener | 128/79 |
| 4,378,008 | 3/1983 | Osbon, Sr. | 128/79 |

FOREIGN PATENT DOCUMENTS

| | | | |
|---|---|---|---|
| 260938 | 9/1912 | Fed. Rep. of Germany | 128/79 |
| 476413 | 5/1929 | Fed. Rep. of Germany | 128/79 |
| 835637 | 2/1952 | Fed. Rep. of Germany | 128/79 |
| 923695 | 1/1955 | Fed. Rep. of Germany | 128/79 |

*Primary Examiner*—Gene Mancene
*Assistant Examiner*—Cary E. Stone
*Attorney, Agent, or Firm*—Stetina and Brunda

[57] ABSTRACT

A sexual erection prosthesis and method of use is disclosed adapted to artificially activate and maintain the penal erection state in human males. The system includes a flexible relatively supple prosthetic device which is sized to encircle the male penis and incorporates an expansible diaphrahm adapted to provide localized constrictive engagement against the penis. The system additionally includes an artificial vascularization assist device which is utilized in combination with the tubular member to obtain hydraulic blood pressure within the penis as well as an insertion device to aid in the placement of the device upon a penis. The system permits the rapid release of the constriction at a desired time to prevent self-injury to the user.

3 Claims, 9 Drawing Figures

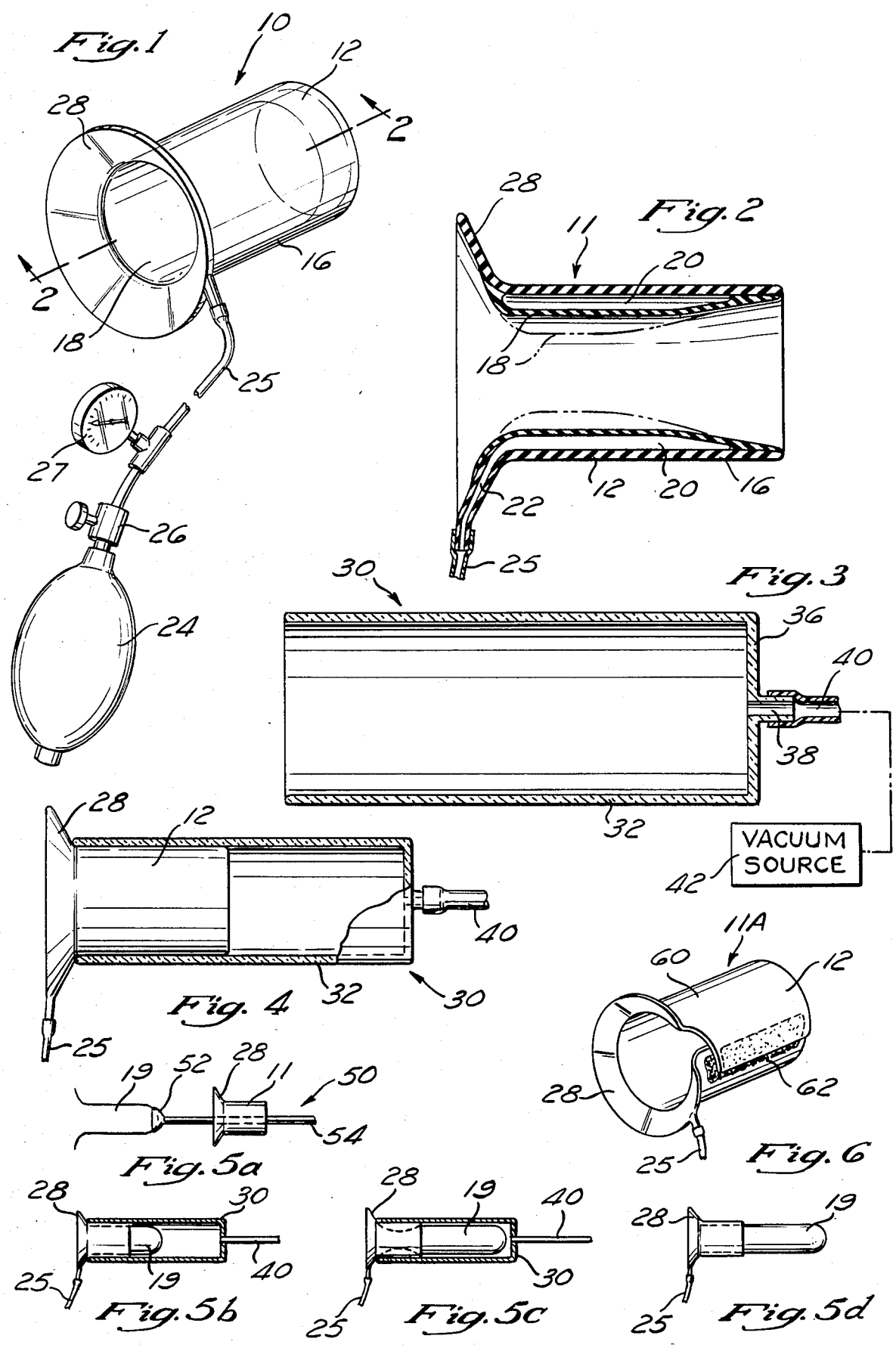

SEXUAL ERECTION PROTHESIS AND METHOD OF USE

BACKGROUND OF THE INVENTION

The present invention relates generally to the field of human medical prosthetics and, more particularly, to a human prosthesis for physiologically and artifically activating and maintaining the penal erection state in human males.

Generally speaking, stimulation of the specific human brain centers associated with sexual response elicits the firing of autonomic nerve impulses which have an effect upon the human male's genitalia. Apparently, upon the receipt of these nerve impulses, a vascularization which increases the blood flow into the penis and/or a concurrent vaso-constriction of a blood net at the base of the human penis which rstricts the flow of blood from said structure, causes a dilation and expansion of the penal vascular system. This resultant increased inflow, i.e. controlled hydraulic action and controlled restricted outflow of blood within the penis causes an enlargement or erection of the penis. However, in some case, for various reasons such as the mental inability to elicit such nervous activation and/or the physical inability to cause increased vascularization and/or vaso-constriction of the blood network which would naturally result in the erection state, some human males are temporarily or permanently unable to achieve this physiological condition. This will have obvious adverse psychological and/or marital implications.

As a result of this problem, many proposed solutions have been introduced in the prior art which may be generally classified as either surgical or uncontrollable artificial rigid prosthesis devices. In the surgical devices an artificial prosthesis is inserted, i.e. implanted directly into the interior of the penis. This inserted member may take the form of a semi-rigid rod or as an inflatable column; however, both surgical solutions involve the implantation of the respective device into the male anatomical structure, a solution which most males find intimidating. Furthermore, such prior art surgical solutions have additional deficiencies limiting their use such as: (1) the semi-rigid member always remaining in the erect state; and (2) the inflatable member having a high susceptibility to mechanical failure. This latter problem invariably requires subsequent revisional surgery. Thus the surgical prior art solutions have proven undesirable and do not provide a popular or viable solution to the impotency problem.

The prior art non-surgical prosthetic devices are of three types (1) spring clip devices; (2) rigid or stretchable band devices; and (3) exo-skeletal devices. The spring clip devices attempt to invoke a vaso-constrictive effect by a simple clamping of the penis. However, these devices generally apply sufficient pressure to restrict blood flow so as achieve the desired erect physiological state. In contrast, if the clips are modified or designed to achieve the desired vaso-constrictive functions, the constrictive pressure applied may cause pain to the user as well as restrict seminal flow. As a result, this device does not provide a viable solution to the problem presented.

The second prior art type prosthetic device generally suffers from the same deficiencies as the first prior art type devices in that they are uncomfortable or ineffective. In addition, there are generally no means to vary nor quickly release the amount of restrictive pressure to be applied. Furthermore, if a variable pressure is achieveable, there is no means to effectively reproduce the amount of varied constrictive pressure applied.

Finally, in the last type of prior art prosthetic device, the penis is inserted into a rigid sheath which directly provides the mechanical structural support. However, this type of prior art device suffers from the deficies of: (1) a total loss of penile tactile sensations as a result of the encapsulation of the user's penis; (2) irritation to the user's genitalia resulting from frictional forces within the exo-skeletal structure; and (3) the restriction or elimination of the ejaculation resulting from the the enclosure of the user's penis. Modifications to this type of prior art device which provide for openings at both ends of the tubular structure or provide an inflatable insert to maintain structural attachment to the user's penis still require sufficient length to provide the mechanical support to simulate the erect state. The tactile penile sensations experienced by the user are generally non-existent. Thus, the prior art devices do not provide a viable solution to the impotency problem.

Therefore, there exists a need in the art for a device which artifically simulates the natural biological functions of the human physiology so as to elicit an erection state in the human male and subsequently control and maintain the erection state throughout intercourse without having to resort to surgery and/or undesirable rigid uncontrollable exo-skeletal prior art devices.

SUMMARY OF THE INVENTION

The present invention specifically overcomes these deficiencies in the prior art by providing an inexpensive non-surgical means to foster or facilitate a male's own physiological mechanisms to artifically achieve, completely control and maintain the erect state.

To incorporate the male subject's present physiological system, the present invention comprises a flexible, relatively supple prosthetic device which is sizes to fit over, i.e. encircle, the male penis. The prosthetic device includes an inflatable air tight cavity formed by an expansive diaphragm. By monitoring and selectively pumping air into an air tight cavity formed by the diaphragm, a localized constrictive engagement between the diaphragm and the surface of the human subject's penis is facilitated. By such engagement, a vaso-constricting effect is applied to the subject's penis in order to restrict the outflow of blood from the penis and thus envoke the penis' natural hydraulic pressure system. Furthermore, since the prosthetic device extends over only a short portion of the base of the penis, the natural physiological erect state is effected without a total sheathing of the penis. By minimizing the sheathing, there is no impairment of the penis' tactility. Furthermore, by incorporating a pressure gauge and release valve, the danger of overly constrictive engagement is avoided. In addition, the pressure gauge ensures the reproducibility of the desired physiological state by quantizing the constrictive pressure applied to the subject's penis. Thus, in contrast to the prior art, the present invention provides a safe means to achieve and maintain the physiological state of erection without depriving the human subject of the sensations attendant with intercourse.

In addition, where the human subject's own vascularization mechanisms are inefficient or unable to provide the sufficient amount of blood into the penis to achieve the desired erect physiological state, a means is provided for use in conjunction with the prosthetic device of the present invention in order to artificially provide the subject's vascularization. This means for artificially increasing the vascularization of the penis is comprised of a cylindrical tube which is sized to fit over the penis and prosthetic device of the present invention and wherein by the application of a vacuum to the cylindrical tube, an increased vascularization and the concurrent vaso-constriction of the exiting blood by use of the present invention's prosthetic device results in the achievement of the desired physiological erect state.

In addition, wherein the anatomical structure is sometimes difficult to fit through the cylindrical portions because of the flacid state of the penis, a means is provided to assist in the insertion of the subject's penis through the aforementioned devices of the present invention.

Thus, the present invention provides an overall system which is capable of either controllably maintaining an erection or in addition, artificially stimulating, controlling and maintaining an erection in a simple, safe, comfortable manner.

BRIEF DESCRIPTION OF THE DRAWINGS

These as well as other features of the present invention will beocme more apparent upon reference to the drawings herein:

FIG. 1 is a depiction of the sexual erection prosthesis of the present invention.

FIG. 2 is a cross-sectional side view of FIG. 1 taken along the lines 2-2 of FIG. 1.

FIG. 3 is a cross-sectional schematic view of the vacuum assist structure of the present invention.

FIG. 4 is a depiction of the vacuum assembly in use with the sexual erection prosthesis of the present invention.

FIGS. 5a through 5c depict a method of use of the present invention; and

FIG. 6 is a perspective of a second embodiment of the sexual erection prosthesis of the present invention.

DETAILED DESCRIPTION OF THE PREFERRED EMBODIMENT

Referring to FIGS. 1 through 5, there is shown the sexual prosthesis system of the present invention designated generally by the numeral 10. The overall sexual prosthesis system 10 is composed of a sexual erection prosthesis device 11, a vascularization device 30 and an insertion aid device 50.

Referring to FIGS. 1 and 2, a more detailed construction of the sexual prosthesis device 11 may be described. The sexual prosthesis device 11 is composed of a tubular sleeve element 12 which is preferably formed of a fabric reinforced elastomeric material such as rubber to possess a soft yet firm structural configuration. The sleeve element 12 includes a cylindrical central portion 16 which terminates in an increased diameter flared flange portion 28 at one end thereof. An expansible tubular element or diaphragm 18 is positioned within the interior of the sleeve element 12 and is fixably mounted at opposite ends to the inner wall of the cylindrical portion 16 so that an air tight circumferentially extending cavity 20 is formed between the diaphragm 18 and the cylindrical portion 16.

In the preferred embodiment, the diaphragm 18 is formed of a thin walled elastomeric rubber material which is readily deformable compared to the reinforced walled tubular sleeve element 12. The inlet opening 22 extends through the flange portion 28 of the device 11, so as to be in flow communication with the cavity 20. A flexible conduit 25 is fixedly securred to the opening 22 at the flange portion 28 and is connectable to an air pressure gauge 27, a valve 26 and a hand pump mechanism 24. The incorporation of the air pressure gauge provides a means to more closely monitor the pressure within the cavity 20 so as to prevent injury. The pressure guage also provides a mean to quantize the amount of air inserted into cavity 20 to ensure the reproducability of any amount of constrictive engagement applied to the penis and thus the degree of the physiological erect state. The valve 26 is preferably a combination check and on-off valve. As will be recognized, by closing the valve 26, and by manually depressing the hand pump or bulb 24, a quantity of air, i.e. a fluid medium is supplied to the cavity 20 via the conduit 25 and opening 22. Due to the relative thickness of the diaphragm 18 and the walls of the sleeve element 12, as a sufficient quantity of air is pumped into the cavity 20, the diaphragm 18 radially expands from its full line position to its phantom line position as shown in FIG. 2.

In use, the tubular sleeve element 12 serves to artifically maintain an erection upon a male user, not by directly providing the mechanical structural support but by envoking and maintaining the penis structure's own hydraulic action. Thus, the tubular sleeve element 12 serves to artificially maintain an erection upon a male user and is therefore primarily suited for use in those situations where an erection can be physiologically produced by a male but cannot be physiologically maintained. In such applications, the tubular sleeve device 11 is positioned upon the penis 19 as schematically depicted in FIG. 5a and is subsequently positioned such that the flange portion 28 of the device 11 abuts or contacts the base of the penis 19. As will be recognized, the positioning of the device 11 can be accomplished by manually stretching the penis 19 so as to reduce its effective diameter. When a sufficient amount of blood has entered into the penis 19 through normal physiological response to achieve the desired erect physiological state, the male user may throttle the valve 26 to a closed position and repeatedly manually depress the bulb pump 24 so as to force a quantity of air into the cavity 20. As the cavity 20 is filled, the diaphragm 18 expands radially inward within the interior of the tubular element 12 to compress tightly about the penis 19.

Preferably, the diaphragm 18 engages the penis 19 at a specifically localized portion of the penis 19 located adjacent the base thereof, which provides a localized vaso-constriction by constrictive engagement of the diaphragm 18 against the penis 19. When a sufficient amount of constriction has been applied, the check valve 26 holds the pressure whereby the constriction of the diaphragm 18 against the penis 19 is maintained. The male user may subsequently engage in intercourse while ensuring the erect state of the penis 19 will be maintained. Before ejaculation during intercourse, the valve 26 may be manually manipulated to an open position wherein the air maintained within the chamber 20 is vented to atmosphere to allow unrestricted ejaculation without the possiblity of self-injury. Subsequently, the tubular sleeve element 12 may subsequently be manually removed from the penis 19 upon completion of intercourse.

In the preferred embodiment, the tubular sleeve device 11 is generally formed having a length of approximately two to two and one-half inches such that a large percentage of the length of an erect penis 19 is not enveloped within the sleeve 12. Furthermore, the sleeve element 12 may be of a varying diameter to accomodate the divergent sizes of penises characteristic of human anatomy. Further, due to the tubular element 12 being formed of a relatively soft and supple material, use of the same does not unduly detract from the intercourse experience nor pose any significant safety hazards to the intercourse participants.

In addition, the present invention contemplates the selective application of varying pressure or restriction upon the penis. This result is made possible by varying the wall thickness of the diaphragm 18 axially along its length such that during expansion of the diaphragm 18 the radial extension of the diaphragm 18 will not be uniform but rather will vary in an amount proportional to the variance in the wall thickness. Thus, by proper design, the sleeve element 12 can be fitted to provide optimum constrictive results for an individual user without adversely affecting sexual performance.

In those instances where the physiological response of the male user is insufficient to provide a sufficient amount of blood into the penis to achieve a desired physiological erect state, the present invention provides a vascularization device 30 which is utilized in combination with the sexual prosthesis device 11 to artificially provide hydraulic pressure to the penis 19. The construction of the artificial vascularization assist device 30 is depicted in FIG. 3 and comprises a vacuum chamber or cylindrical tube 32 formed having a diameter slightly greater than the outside diameter of the central portion 16 of the tubular element 12. One end of the cylindrical tube 32 is formed in an open configuration while the opposite end includes an end wall 36 to form a closed end configuration. The length of the cylindrical tube 32 is sized to be substantially greater than the length of the tubular element 12 such that the cylindrical tube 32 can be telescopingly positioned over the central portion 16 of the prosthesis device 11. The end wall 36 includes an annular port 38 which is sized to receive a conduit or flexible line 40. The conduit 40 extends from the port 38 to a pressure gauge and continues to the vacuum source 42 illustrated schematically in FIG. 3. As will be recognized, when the vacuum source 42 is initiated, a vacuum is applied to the interior region of the cylindrical tube 32 through the vacuum port 38.

The use of the artificial vascularization assist device 30 of the present invention is depicted in FIGS. 5b and 5c. Initially, the sexual prothesis device 11 must be inserted upon the penis 19 in a manner previously described. However, in those instances where manual elongation of the penis is difficult to effectuate, an insertion device 50 of the present invention may be utilized. Basically, this insertion device 50 comprises a suction cup-like member 52 which may be attached to a suitable length of flexible conduit 54. The conduit 54 may be selectively attached to the vacuum source 42 such that upon activation of the vacuum source, a moderate suction is developed at the suction cup member 52.

Preparatory to use of the insertion member 50, the sexual erection prosthesis device 11 may be positioned along the length of the conduit 54 and the suction cup member 52 may be positioned upon the end of the penis 19 as depicted in FIG. 5a. Activation of the vacuum source 42 causes the application of a moderate vacuum to the end of the penis 19 which maintains the suction cup member 52 upon the penis 19. The flexible conduit 54 may then be pulled away from the penis 19 causing an elongation of the penis 19 whereby the prosthesis device 11 may be reciprocated along the length of the penis 19 and firmly seated at its base.

With the prosthesis device 11 positioned upon the penis 19, the vacuum source 42 may be deactivated whereby the vacuum upon the suction cup member 52 is disconnected and the insertion device 50 may be removed from the penis 19. Subsequently, the artificial vascularization assist device 30 may be positioned over the penis 19 and prosthesis device 11 as depicted in FIG. 5b wherein the open end of the vascularization assist device 30 abuts the flange 28 of the prosthesis device 11. The activation of the vacuum source 42 thereby causes vacuum pressure to be exerted within the interior of the cylindrical member 30 and causes a complete seating of the end of the cylindrical member 30 upon the flange 28 to eliminate any air flow entering into the tubular member 30 from its open end. The continued application of the vacuum source 42 within the interior of the cylindrical member 30 causes blood to be artifically induced into the penis 19 thereby forming a hydraulic action which causes the penis to enlarge into an erect state. The prosthesis device 11 can then be manipulated in a manner previously described to cause a vaso-constriction of the penis 19 to maintain the induced hydraulic blood pressure within the penis 19. Subsequently, the vacuum source 42 may be discontinued and the artificial vascularization assist device 30 can be rapidly removed from the prosthesis device 11. Intercourse may then be effectuated without the fear of failing to maintain the erection for a sufficient period of time. Just prior to ejaculation, the valve 26 is manipulated to release the vaso-constriction, because there is a physiologically increased vascularization just prior to the state of ejaculation. This increased pressure will by itself maintain the erect state. Furthermore, continued vaso-constriction may result in trauma if maintained during this increased vascularization period. However, the quick release valve 26 of the present invention allows for rapid venting of the cavity 20 and thus prevents such trauma from occurring during ejaculation.

As such, it will be recognized that the present invention comprises a significant improvement over the prior art devices by providing means for maintaining or alternatively obtaining and maintaining an erection by use of a particular system which is relatively easy to install and can be utilized without harm to the user.

Referring to FIG. 6, an additional embodiment of the sexual erection prosthesis device 11a of the present invention is depicted which is formed in a manner analogous to the embodiment of FIG. 1 except that the central tubular portion 16 and flange portion 28 is split to allow the device 11a to be wrapped about the penis 19. Referring more particularly to FIG. 6, it can be seen that in this embodiment, the tubular portion 60 is provided with a velcro fastener 62 which when the device is wrapped about the penis 19 may be engaged to maintain the same about the penis. This particular embodiment of the invention is particularly suited for large penis anatomies as well as facilitates easier placement of the device 11a upon the penis 19.

In conclusion, the present invention provides a means to effect a physiological state of erection in a human male as well as maintain the physiological state for a desired length of time. As a result, the individual male subject is able to achieve the natural physiological state of erection without having to result to surgical implantation techniques or rigid exo-skeletal structures which have heretofore been utilized in the art. Having described a preferred embodiment of the present invention, various modifications will now become apparent from the specification and the drawings which clearly are contemplated within the scope of the appended claims.

What is claimed is:

1. A method of artifically enhancing the physiological condition of a male erection comprising the steps of:

positioning a tubular member over the penis of a user, said tubular member having an expansible portion disposed within its interior; and selectively admitting a pressurized fluid to said expansible portion to enlarge said expansible portion to contact the penis of a user in constrictive engagement sufficient to maintain the penis in an erect state; said pressurized fluid admitting step comprising manually pumping a quantity of pressurized fluid into a cavity formed within said tubular member, and said positioning step comprising the steps of elongating the penis of the user to reduce the diameter of the penis; and reciprocating said tubular member along the length of the penis to abut the base of the penis; said elongating step comprising the steps of:

attaching a cup member to the end of the penis;

applying a vacuum to said cup member through an elongate conduit; and manually pulling said conduit to moderately stretch the penis of the user.

2. A method of artifically enhcancing the physiological condition of a male erection comprising the steps of:

positioning a tubular member over the penis of a user, said tubular member having an expansible portion disposed within its interior; artificially vascularizing the penis of the user; and selectively admitting a pressurized fluid to said expanisble portion to enlarge said expanisble portion to contact the penis of a user in constrictive engagement sufficient to maintain the penis is an erect state.

3. The method of claim 2 wherein said artificial vascularizing step comprises the steps of:

positioning a vacuum vessel over the end of the penis and abutting the same against one end of said tubular member.

* * * * *